United States Patent
Ploetz

[19]

[11] Patent Number: 6,005,907
[45] Date of Patent: *Dec. 21, 1999

[54] METHOD AND APPARATUS FOR PRODUCING TOMOSYNTHESIS EXPOSURES EMPLOYING A REFERENCE OBJECT COMPOSED OF A NUMBER OF SUB-OBJECTS

[75] Inventor: Josef Ploetz, Bensheim, Germany

[73] Assignee: Sirona Dental Systems GmbH & Co. KG, Bensheim, Germany

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/859,813
[22] Filed: May 19, 1997

[30] Foreign Application Priority Data

May 17, 1996 [DE] Germany .............................. 196 19 915

[51] Int. Cl.$^6$ ....................................................... G01T 1/00
[52] U.S. Cl. .................................................. 378/2; 378/162
[58] Field of Search ............................................ 378/2, 162

[56] References Cited

U.S. PATENT DOCUMENTS

| 5,070,454 | 12/1991 | Griffith . | |
|---|---|---|---|
| 5,299,254 | 3/1994 | Dancer et al. | 378/162 |
| 5,359,637 | 10/1994 | Webber . | |
| 5,598,454 | 1/1997 | Franetzki et al. . | |

FOREIGN PATENT DOCUMENTS

| 0 479 618 | 4/1992 | European Pat. Off. . |
|---|---|---|
| WO 93/22893 | 11/1993 | WIPO . |

*Primary Examiner*—Craig E. Church
*Attorney, Agent, or Firm*—Hill & Simpson

[57] ABSTRACT

In a method and an apparatus for producing a tomosynthesis exposure of an examination subject, an X-ray beam is directed at the subject from different directions and a reference object composed of at least two sub-objects is disposed in the X-ray beam together with the subject. X-rays attenuated by the reference object composed of at least two sub-objects and the examination subject are received by a radiation receiver, which generates electrical signals corresponding to X-rays incident thereon, from which a tomosynthesis image is constructed.

26 Claims, 3 Drawing Sheets

METHOD AND APPARATUS FOR PRODUCING TOMOSYNTHESIS EXPOSURES EMPLOYING A REFERENCE OBJECT COMPOSED OF A NUMBER OF SUB-OBJECTS

BACKGROUND OF THE INVENTION

1. Field of the Invention

The present invention is directed to an X-ray diagnostic apparatus for a tomosynthesis, and in particular to an apparatus of the type employing a reference object in the radiation beam proceeding from the radiation emitter.

2. Description of the Prior Art

PCT application WO 93/22 893 discloses a method with which it is possible to reconstruct an exposure of an examination subject without the projection angle α and the geometrical arrangement of the radiation emitter and radiation receiver and the focal plane being known. According to this method, a reference object of radiation-absorbing material having a known size and a known spacing from the radiation receiver is provided in the region of the radiation receiver, this reference object being projected onto the radiation receiver in every individual projection. The geometrical arrangement and the two-dimensional projection angle α for each individual projection can be determined on the basis of the two-dimensional spatial imaging of the reference on the radiation receiver.

A holder for positioning a radiation emitter of an X-ray diagnostic apparatus for tomosynthesis is disclosed in German OS 44 14 689, corresponding to U.S. Pat. No. 5,598,454. A bracket is coupled to the holder, at which —as viewed in the radiation propagation direction —a spherical reference object is arranged in front of the examination subject and a radiation receiver is arranged behind the examination subject. The spacing of the radiation from the reference object and from the radiation receiver, as well as the angle α of a ray beam emitted by the radiation emitter relative to a reference axis of the holder mechanism, are prescribed by the holder. It is also known to arrange the radiation source so as to be adjustable in a housing to which a positioning means for the reference object and the radiation receiver can be coupled.

In such known tomosynthesis systems, because the reference object is disposed in front of the examination subject and is mounted on a bracket connected to the holder for the radiation receiver, the reference object can constitute a nuisance or an impediment in setting up the apparatus and conducting the examination.

SUMMARY OF THE INVENTION

It is an object of the present invention to provide a method and an apparatus for producing tomosynthesis exposures which allow a precise acquisition of the geometrical arrangement of the radiation emitter, the radiation receiver and the examination subject, and which create more flexible and efficient possibilities of fashioning the apparatus, positioning the examination subject and generating tomosynthesis exposures from the signals of the radiation receiver.

The above objects are achieved in accordance with the principles of the present invention in a method and an apparatus for producing a tomosynthesis exposure of an examination subject having a radiation emitter and a radiation receiver, with a reference object disposed therebetween in the path of a radiation beam emanating from the radiation emitter, wherein the reference object is composed of at least two sub-objects.

An advantage of the invention is that a reference object that is composed of at least two sub-objects is employed. Not only the spacing of the radiation emitter from the radiation receiver, but also the incident angle (projection angle) and the irradiation direction can be very exactly determined. Rotation of the radiation receiver relative to the reference object can also be exactly acquired. The reference object can also be directly connected to the radiation emitter and need not be coupled to the radiation receiver.

In the inventive apparatus, the sub-objects are fashioned beam-like and are arranged cruciatly or apparatus alternatively, at least three sub-objects whose arrangement relative to one another deviates from a straight line are provided. The sub-objects can then be fashioned sphere-like or disk-like and form a geometrical (polygonal) body. In an embodiment wherein the sub-objects differ in terms of their radiation absorption, then the irradiation direction can be determined in an especially exact way.

DESCRIPTION OF THE PREFERRED EMBODIMENTS

Figure 3:
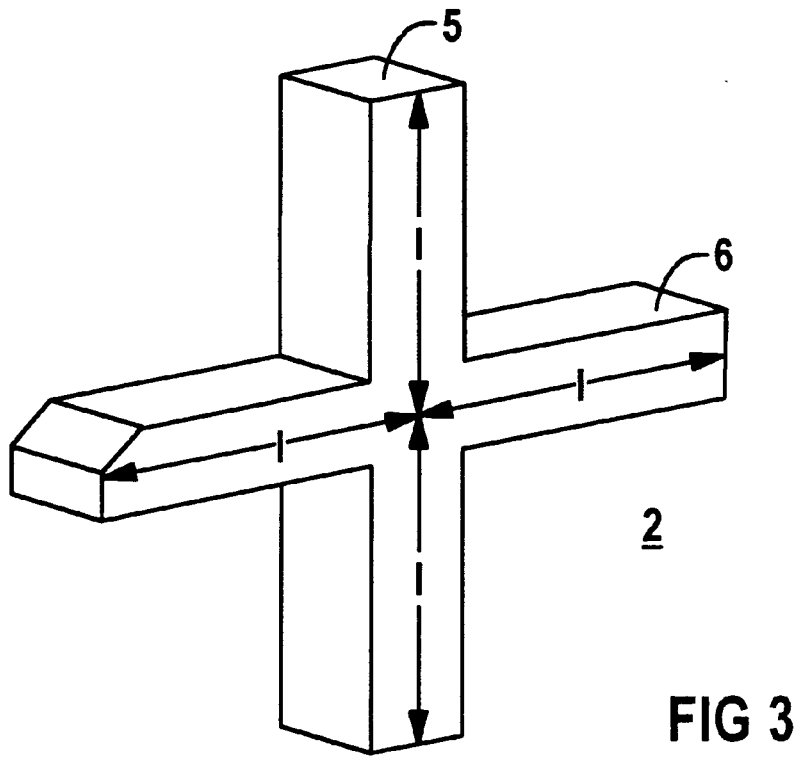
FIG. 3 shows a first exemplary embodiment of an inventive reference object of the X-ray diagnostics apparatus according to FIG. 1 or FIG. 2.
Figure 4:
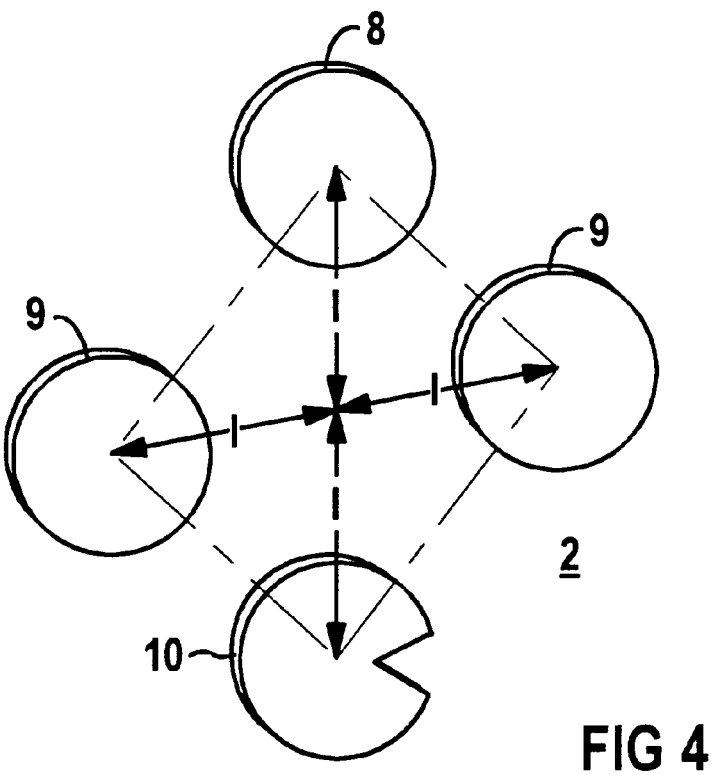
FIG. 4 shows a second exemplary embodiment of an inventive reference object of the X-ray diagnostics apparatus according to FIG. 1 or FIG. 2.

For the implementation of the inventive method for producing a tomosynthesis exposure of an examination subject, an X-ray diagnostic apparatus has a radiation emitter, especially a radiation source 1, a reference object 2 and a radiation receiver 3. According to FIG. 1, the reference object 2 and the radiation source I have a fixed reference relationship to one another, for example via a holder 11. The signals generated by the radiation receiver 3 upon transirradiation of the reference object 2 and the examination subject are supplied to an image-generating computer 4 that calculates the distance from the radiation receiver 3 and from the examination subject as well as the irradiation angle (projection angle) and the irradiation direction from the signals of the reference object 2 and, in combination with the signals of the examination subject produces image signals of a tomosynthesis exposure. According to the inventive method for producing a tomosynthesis exposure, a reference object 2 is employed that is composed of at least two sub-objects 5 and 6 that are fashioned beam-like and cross one another according to a first version (FIG. 3). According to a second version (FIG. 4), a reference object 2 is employed that is formed at least three sub-objects 7, 8, 9 and 10 whose arrangement relative to one another deviates from a straight line. For example, these sub-objects 7, 8, 9 and 10 can be fashioned spherically, disk-like, beam-like, rod-like or cylindrically. Preferably, at least one sub-object 6 or 10 differs at least in a sub-region from the other sub-objects 5, 7, 8 and 9 in terms of radiation absorption, so that the projection directions can be exactly determined when the dimensions of the reference object or of the sub-objects 5,6,7,8,9 and 10 are known. The difference in terms of radiation absorption can be achieved by cut-outs or incisions at the sub-objects 6 or 10, or by making their thickness, length, spacing from one another, material or shape different from the other sub-objects.

Figure 1:
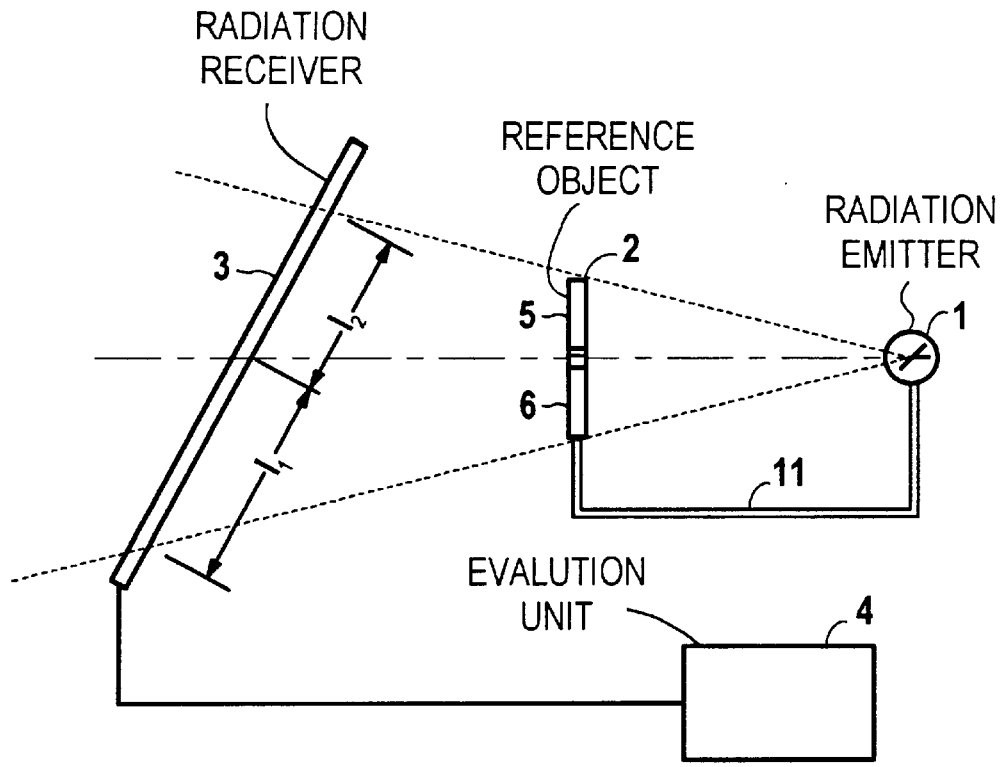
FIG. 1 is a schematic illustration of an X-ray diagnostics apparatus for tomosynthesis, constructed and operating in accordance with the present invention, wherein a reference object has a fixed reference relationship to the radiation emitter, to which it is directly connected.
Figure 2:
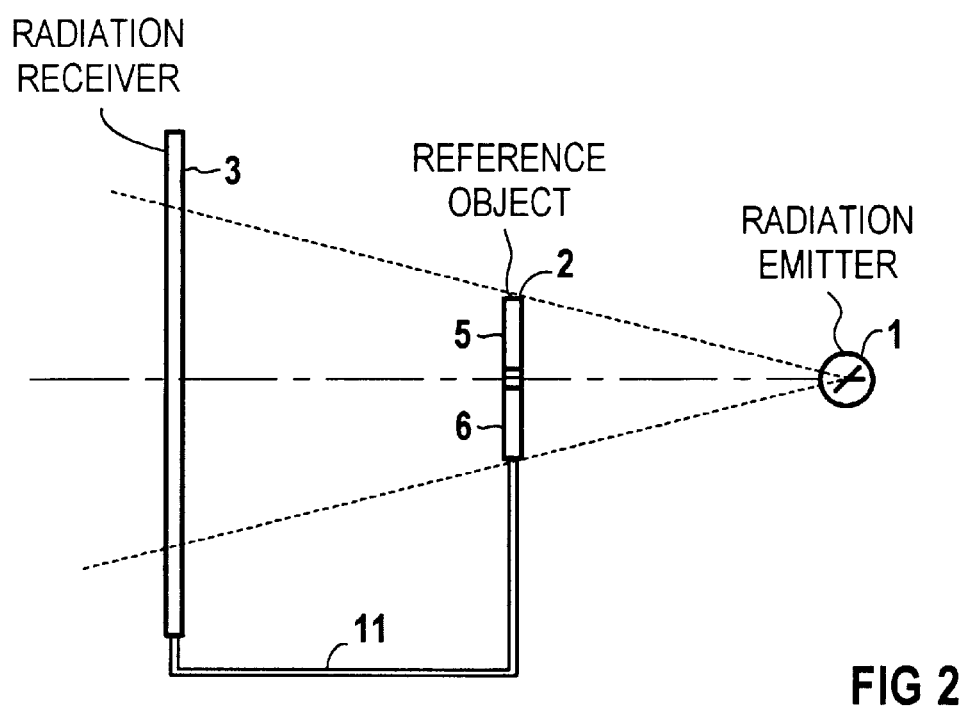
FIG. 2 is a schematic illustration of an X-ray diagnostics apparatus for tomosynthesis, constructed and operating in accordance with the present invention, wherein the reference object has a fixed reference relationship to the radiation receiver, to which it is directly connected.

The X-ray diagnostic apparatus shown in FIG. 2 differs from the X-ray diagnostic apparatus shown in FIG. 1 in that the reference object 2 has a fixed reference relationship to the radiation receiver 3, to which it is connected, for example via a holder 11.

Figure 5:
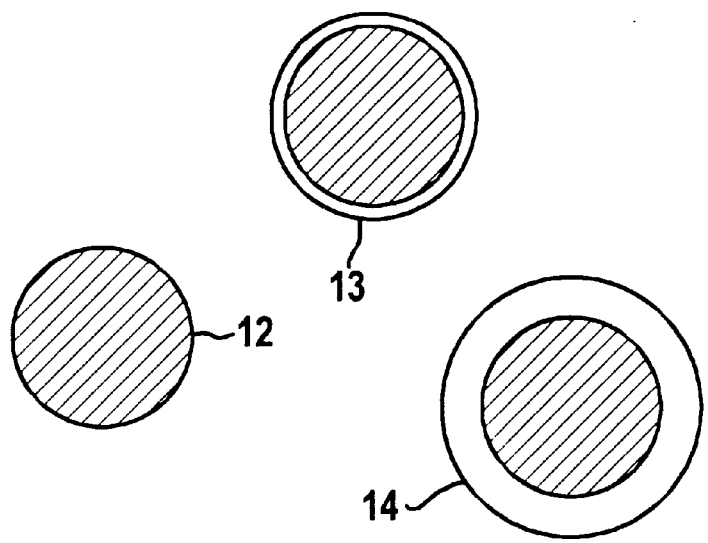
FIG. 5 shows a third exemplary embodiment of an inventive reference object of the X-ray diagnostics apparatus according to FIG. 1 or FIG. 2.

In an embodiment of the method and apparatus, at least three sub-objects 12,13 and 14 that differ in view of the radiation absorption are provided, their arrangement relative to one another deviating from a straight line. For example, spheres can be provided for this purpose, their radiation absorption differing at least in sub-regions, for example due to marking members applied to the spheres, and/or by their projection onto the radiation receiver 3 at least approximately known with respect to the location. As shown in FIG. 5, a first sub-object 12 is fashioned, for example, as a solid sphere. Second and third sub-objects 13 and 14 fashioned, for example as spheres each having an edge that noticeably differs from the core in view of the radiation absorption. The second and third sub-objects 13 and 14 differ in terms of their size or thickness at the edge. A particular advantage is thereby achieved that, given employment of such a reference object that has a fixed reference relationship to the examination subject, the position and attitude of the examination subject as well as of the radiation source 1 relative to the radiation receiver 3, the geometrical arrangement and the two-dimensional projection angle can be determined, so that a tomosynthesis exposure of the examination subject can be reconstructed without the examination subject having to be coupled to the radiation receiver 3 or the radiation source 1, the radiation source 1 and the radiation receiver 3 or without having to be coupled to one another. A further advantage is that the sub-objects 12,13 and 14 of the reference object can be arranged in arbitrary relative positions at the examination subject independently of one another.

The position of the radiation source 1 can be defined first in the coordinate system of the radiation receiver 3 on the basis of the interpretation of the imaging locations of the sub-objects on the radiation receiver 3, and the distortion in terms of degrees, and the direction of its radiation shadow which occur given an oblique projection. When the position of the radiation source 1 is known, then, given a known size of the sub-objects, conclusions about their position can be made from the imaging scale. An initial position of the examination subject is thus defined with a first exposure with an arbitrary irradiation direction, and later changes in position can be unambiguously identified.

Figure 6:
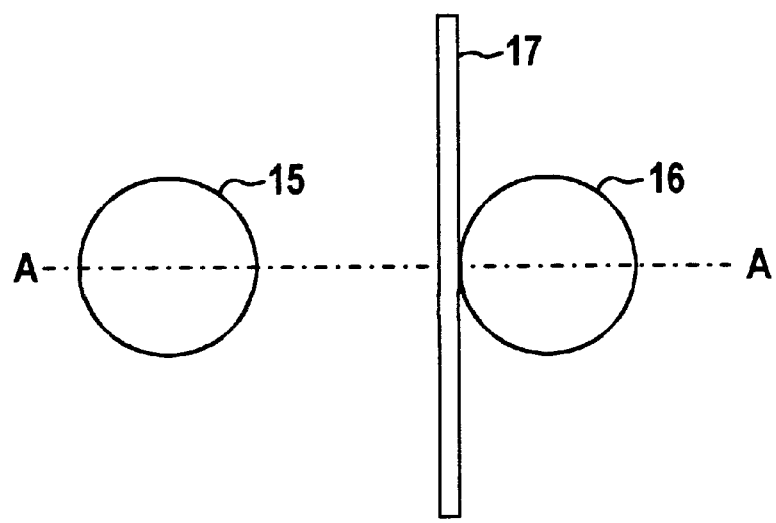
FIG. 6 shows a fourth exemplary embodiment of an inventive reference object of the X-ray diagnostics apparatus according to FIG. 1 or FIG. 2.

In a modification of the method, a reference object, formed of only two sub-objects, for example spheres, differing in terms of their radiation absorption and a third sub-object that is fashioned beam-shaped or rod-shaped, can be employed. An exemplary embodiment of such a reference object is shown in FIG. 6, which shows a sub-object 15 fashioned as a sphere, a beam or rod shaped sub-object 17, and another, sub-object 16 fashioned as a sphere. The position of the radiation source 1 can thus already be determined using only two differing sub-objects 16 and 17. A rotation of the examination subject around the connecting line of these sub-objects 15 and 16 can be determined by evaluation of the projection distortion of the two sub-sections of the beam or rod shaped sub-object 17.

When more than three sub-objects are employed in the evaluation, then the precision of the position and angle determination can be improved and redundancy can be achieved when, for example, the images of individual sub-objects cannot be evaluated because for example, they are superimposed with highly absorbent structures of the examination subject.

Although the present invention has been described with reference to a specific embodiment, those of skill in the art will recognize that changes may be made thereto without departing from the scope and spirit of the invention as set forth in the appended claims.

I claim as my invention:

1. A method for producing a tomosynthesis exposure of an examination subject comprising the steps of:

directing an X-ray beam at an examination subject from an X-ray emitter from different directions with said X-ray emitter at different positions respectively defining said different directions;

forming a reference object of at least two sub-objects and placing said reference object composed of at least two sub-objects in said X-ray beam;

disposing a radiation receiver in said X-ray beam behind said subject and said reference object with no fixed spatial relation to said reference object;

receiving X-rays from said X-ray emitter, attenuated by said reference object and said subject, at said radiation receiver during a plurality of exposures, each of said exposures being made from one of said different directions, and generating electrical signals for each exposure corresponding to X-rays incident at said radiation receiver; and from said electrical signals, identifying the position of said X-ray emitter during each of said exposures from a location of said sub-objects in each exposure, and generating a tomosynthesis image of said subject.

2. A method as claimed in claim 1 wherein the step of forming said reference object from at least two sub-objects comprises arranging at least three sub-objects relative to each other in an arrangement deviating from a straight line.

3. A method as claimed in claim 1 comprising arranging at least three sub-objects to form a geometrical body.

4. A method as claimed in claim 3 comprising the step of arranging said at least three sub-objects in a crucial shape.

5. A method as claimed in claim 2 comprising forming said reference object of at least three spherical sub-objects.

6. A method as claimed in claim 2 comprising forming said reference object of at least three disk-shaped sub-objects.

7. A method as claimed in claim 1 wherein the step of forming said reference object from at least two sub-objects comprises forming said reference object from at least two beam-shaped sub-objects.

8. A method as claimed in claim 1 wherein the step of forming said reference object from at least two sub-objects comprises forming said reference object from at least two rod-shaped sub-objects.

9. A method as claimed in claim 1 wherein the step of forming said reference object from at least two sub-objects comprises forming said reference object from at least two cylindrical sub-objects.

10. A method as claimed in claim 1 wherein the step of forming said reference object of at least two sub-objects comprises forming said reference object of at least two sub-objects having respectively different radiation absorption characteristics.

11. A method as claimed in claim 1 comprising the additional step of directly connecting said reference object to said radiation emitter with a fixed reference relationship to said radiation emitter.

12. A method as claimed in claim 1 wherein the step of forming said reference object of at least two sub-objects comprises forming said reference object by arranging said at least two sub-objects along a straight line.

13. A method as claimed in claim 12 comprising the additional step of employing two sub-objects having respectively different radiation absorption characteristics.

14. An apparatus for producing a tomosynthesis exposure of an examination subject comprising:
- a radiation emitter which emits an X-ray beam successively proceeding in a plurality of different directions respectively defined by different positions of said radiation emitter;
- a reference object disposed in said X-ray beam and composed of at least two sub-objects;
- a radiation receiver on which said X-ray beam, attenuated by said examination subject and said reference object composed of at least two sub-objects, is incident, said radiation receiver having no fixed spatial relation to said reference object and producing electrical signals corresponding to X-rays incident thereon during a plurality of successive exposures with said radiation emitter respectively in one of said different positions in said successive exposures; and
- means for identifying, from said electrical signals, a position of said radiation emitter during each of said exposures from a location of said sub-objects in each exposure and for producing a tomosynthesis image of said subject.

15. An apparatus as claimed in claim 14 further comprising means for connecting said reference object to said radiation emitter in a fixed reference relationship to said radiation emitter.

16. An apparatus as claimed in claim 14 wherein said reference object comprises at least three sub-objects oriented relative to each other in an arrangement deviating from a straight line.

17. An apparatus as claimed in claim 16 wherein said at least three sub-objects form a geometrical body.

18. An apparatus as claimed in claim 16 wherein said sub-objects are arranged in a crucial shape.

19. An apparatus as claimed in claim 16 wherein said at least three sub-objects each comprise a sphere.

20. An apparatus as claimed in claim 16 wherein each of said at least three sub-objects is disk-shaped.

21. An apparatus as claimed in claim 14 wherein said at least two sub-objects are each beam-shaped.

22. An apparatus as claimed in claim 14 wherein said at least two sub-objects are each rod-shaped.

23. An apparatus as claimed in claim 14 wherein said at least two sub-objects are each cylindrical.

24. An apparatus as claimed in claim 14 wherein each of said sub-objects has respectively different radiation absorption characteristics.

25. An apparatus as claimed in claim 14 wherein said at least two sub-objects are arranged along a straight line.

26. An apparatus as claimed in claim 25 wherein said at least two sub-objects have respectively different radiation absorption characteristics.

* * * * *